United States Patent [19]

Natsubori et al.

[11] Patent Number: 5,105,092
[45] Date of Patent: Apr. 14, 1992

[54] INSPECTING APPARATUS HAVING A DETECTION SENSITIVITY CONTROLLER MEANS

[75] Inventors: Katsutoshi Natsubori, Kawasaki; Nobuhiro Kodachi, Yokohama; Michio Kohno, Tokyo, all of Japan

[73] Assignee: Canon Kabushiki Kaisha, Tokyo, Japan

[21] Appl. No.: 718,909

[22] Filed: Jun. 24, 1991

Related U.S. Application Data

[63] Continuation of Ser. No. 529,546, May 29, 1990, abandoned.

[30] Foreign Application Priority Data

May 30, 1989 [JP] Japan ................................. 1-134796

[51] Int. Cl.$^5$ ........................................... G01N 21/88
[52] U.S. Cl. .................................... 250/572; 356/237
[58] Field of Search ................ 250/214 AG, 234-236, 250/572; 356/237, 431

[56] References Cited

U.S. PATENT DOCUMENTS

| | | | |
|---|---|---|---|
| 2,947,212 | 8/1960 | Woods | 250/572 |
| 3,667,846 | 6/1972 | Nater et al. | 250/572 |
| 3,748,047 | 7/1973 | Millgood et al. | 250/572 |
| 4,342,515 | 8/1982 | Akiba et al. | 356/237 |
| 4,468,120 | 8/1984 | Tanimoto et al. | 356/237 |
| 4,669,875 | 6/1987 | Shiba et al. | 250/225 |
| 4,795,911 | 1/1989 | Kohno et al. | 250/572 |
| 4,831,274 | 5/1989 | Kohno et al. | 250/563 |
| 4,886,975 | 12/1989 | Murakami et al. | 250/572 |

FOREIGN PATENT DOCUMENTS

62-188945 8/1987 Japan.

Primary Examiner—David C. Nelms
Assistant Examiner—S. Allen
Attorney, Agent, or Firm—Fitzpatrick, Cella, Harper & Scinto

[57] ABSTRACT

An inspecting apparatus, for inspecting a surface state of an article to be inspected, includes a zone detecting system for detecting a zone which can cause strong scattering of light; a surface state detecting system for detecting the surface state of the article, the surface state detecting system including a light source for projecting an inspecting light beam to the article, a light scanning mechanism for relatively moving the article and the inspecting light beam so that the article is scanned with the inspecting light beam, and a photoelectric converter for detecting light from the article scanned with the inspecting light beam by the light source and the light scanning mechanism; an inspecting device for receiving an output signal from the photoelectric converter and for inspecting the surface state of the article; and a sensitivity controller for controlling the detection sensitivity of the surface state detecting system on the basis of the detection by the zone detecting system, such that when the inspecting light beam scans the zone, the detection sensitivity of the surface state detecting system is relatively reduced.

8 Claims, 2 Drawing Sheets

INSPECTING APPARATUS HAVING A DETECTION SENSITIVITY CONTROLLER MEANS

This application is a continuation of application Ser. No. 529,546 filed May 29, 1990, now abandoned.

FIELD OF THE INVENTION AND RELATED ART

This invention relates to an inspecting apparatus and, more particularly, to an inspecting apparatus suitably usable for detecting foreign particles or faults on the surface of a reticle or photomask having a pattern, and for being used in semiconductor device manufacturing processes.

Usually, in an IC manufacturing process, a desired lithographic pattern of a reticle or ask is transferred to a semiconductor wafer having a resist coating, through a projection optical system or the like of a semiconductor printing apparatus (stepper or mask aligner).

When a pattern is transferred from a reticle or mask to a wafer coated with a resist, by using a semiconductor printing apparatus, if a fault such as a foreign particle is present on the surface of the reticle or mask, the shape of such a fault is printed on the wafer in addition to the pattern of the reticle or mask. This results in a decrease in the yield of IC manufacture.

Particularly, when a reticle is used in combination with a stepper for printing desired patterns onto the wafer in a step-and-repeat manner, even a single foreign particle on the reticle can be printed onto every zone of the wafer surface.

In consideration thereof, inspection has been carried out to detect the presence/absence of such a foreign particle through photoelectric conversion, as disclosed in U.S. Pat. No. 4,669,875, for example.

However, there still remains a problem. That is, when a reticle with a pellicle frame having a rough surface (typically, a metal rough surface) is to be inspected, there is a possibility that an intense scattered light is produced by the pellicle frame which damages the photoelectric converting means and/or that a resultant intense signal applied to a preamplifier causes erroneous operation of the preamplifier. If this occurs, it is not possible to detect weak light from a foreign particle.

SUMMARY OF THE INVENTION

It is accordingly an object of the present invention to provide an inspecting apparatus for inspecting foreign particles or faults on the surface of an article, wherein, even when an intense scattered light is produced, the detecting means of the inspecting apparatus is not damaged so that, even in such a case, a weak light from a foreign particle can be detected or discriminated.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1:
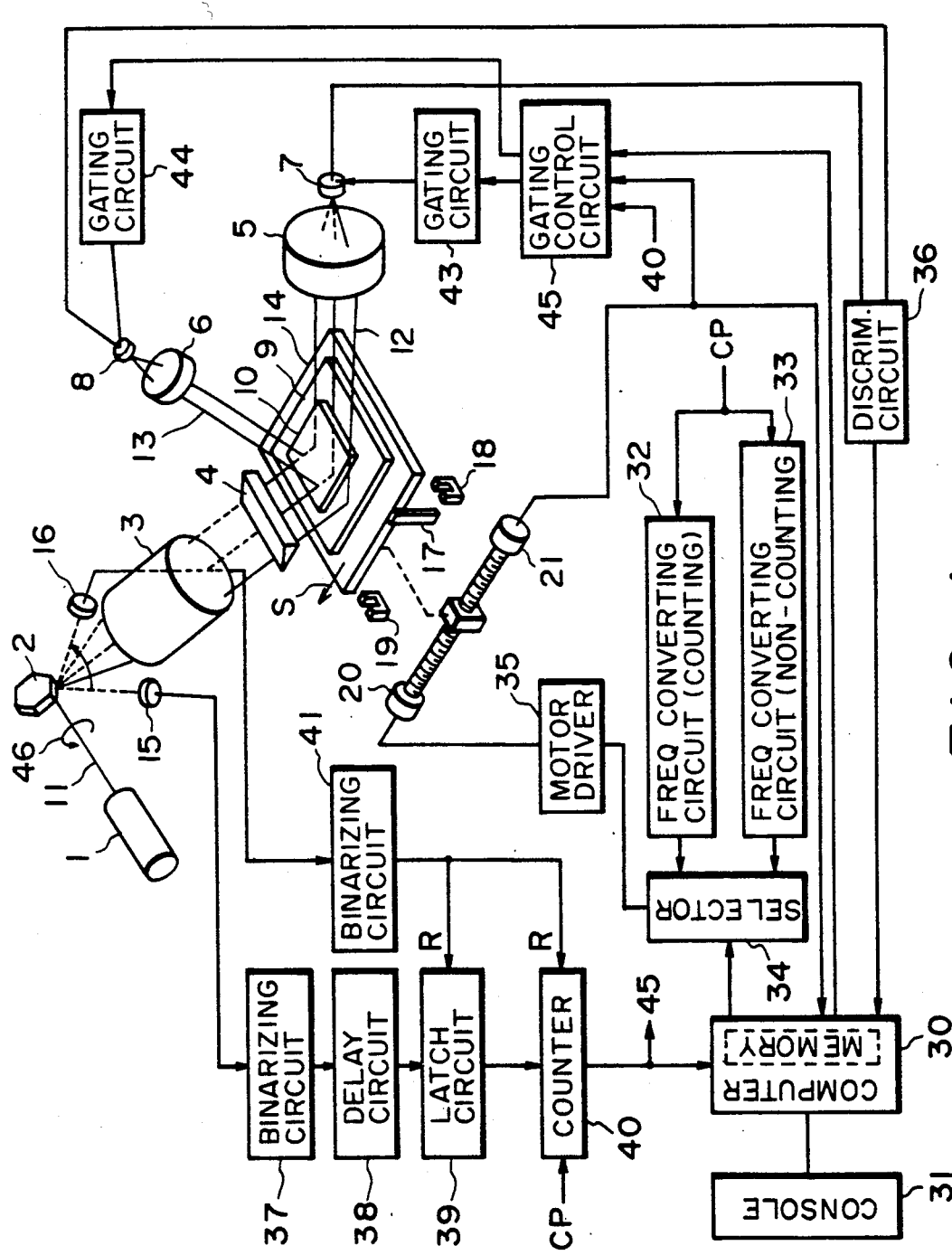
FIG. 1 is a schematic and diagrammatic view showing the structure of a major portion of a foreign particle inspecting apparatus according to an embodiment of the present invention.

In one preferred form of the present invention, to be described later, an inspecting apparatus for inspecting the presence/absence of a foreign particle includes: driving means for rectilinearly feeding an object to be inspected, light projecting optical means for scanning the object with an inspecting light beam, optical detecting means for photoelectrically converting the light from the object, produced by the scan with the inspecting light beam, through photoelectric converting means to produce foreign particle inspection information, first position detecting means for detecting the inspection position upon the object in the direction of movement thereof, second position detecting means for detecting the inspection position upon the object in the direction of the scan of the light beam, sensitivity control means for changing the sensitivity of the photoelectric converting means, with regard to a predetermined region, on the basis of outputs of the first and second position detecting means, storing means for memorizing the predetermined region in preparation, and calculating means for inspecting the predetermined region of the object with a lower sensitivity, before the inspection of the object, to determine the predetermined region.

An example of the object to be inspected is a reticle having a pellicle or pellicles mounted thereto. The region with respect to which the sensitivity of the photoelectric converting means is to be changed is a zone on the frame of the pellicle mounted to the reticle and/or a zone adjacent thereto. With respect to such a zone, the sensitivity control means operates to decrease the sensitivity of the photoelectric converting means. Alternatively, it operates to increase the sensitivity of the photoelectric converting means, with respect to the inside region of the pellicle frame.

For inspection of an object to be inspected, the position upon the object being inspected is monitored by the first and second position detecting means. When such an inspection position is in such a region or a region adjacent thereto, when an intense scattered light is produced by the inspecting light beam, the sensitivity of the photoelectric converting means (e.g., a photomultiplier tube) is controlled so that the received light is photoelectrically converted with a sensitivity lower than that for the other region. In other words, the other region is inspected with higher sensitivity. Accordingly, a weak light from a foreign particle can be detected without being affected by the intense scattered light.

The photomultiplier (PMT) is one of the photoelectric converting elements, and its sensitivity can be changed temporarily in accordance with a method, called "gating". Its timing can be controlled by a control circuit provided in the sensitivity control means. The term "gating" means that the potential difference between electron amplifying electrodes of the photomultiplier is inverted, in sign, as compared with the ordinary amplifying state, for a predetermined time period or, alternatively, it is reduced as compared with the ordinary state.

Referring now to the drawings, FIG. 1 shows the structure of a foreign particle inspecting apparatus according to an embodiment of the present invention. In the structure of this Example, the foreign particle inspection of a reticle is executed in the following manner:

First, a reticle 9 is placed on a stage 14 by means of a hand mechanism, not shown. Laser beam 11 emanating from a laser source 1 is deflected in one direction by a polygonal mirror 2 and, after passing through an $f-\theta$ lens 3 and an aberration correction plate 4 which serves to correct the effect of inclined incidence, the light goes through a pellicle surface and is converged upon the reticle 9 surface. Scattered light 12 at the reticle 9 surface and scattered light 13 at the pellicle 10 surface are collected by condensing lenses 5 and 6, respectively, and they are inputted to photomultipliers 7 and 8, respectively, so that they are converted into electric signals. These electric signals are inputted through a discriminating circuit 36 into a computer 30 and are processed therein. As regards the arrangement for discriminating the presence/absence of a foreign particle, such a structure as disclosed in Japanese Laid-Open Patent Application, Laid-Open No. Sho 62-188945, for example, is usable. On that occasion, the discriminating circuit 36 discriminates the presence/absence of foreign particles on the basis of whether the received signal is larger than a certain slice level.

In FIG. 1, denoted at 15 is a photoelectric converting element for detecting the start point of the scan with the laser beam (inspecting light beam); at 16 is another photoelectric converting element for detecting the end point of the laser beam scanning; at 18 is a photo-switch for detecting the movement start point of the stage 14; and at 19 is another photo-switch for detecting the movement end point of the stage 14. Each photo-switch comprises a light source and a photoreceptor disposed to receive light from the light source. Denoted at 17 is a light blocking plate which is movable as a unit with the stage 14 so as to block the light from the light source of each photo-switch 18 (19) to thereby prevent reception of the light by the corresponding photoreceptor. When the light blocking plate 17 comes to such a switching position that the corresponding photoreceptor produces "zero" output, it is discriminated that the stage is at the movement start point (the movement end point). Denoted at 20 is a pulse motor for moving the stage 14 through a ball screw and nut structure; at 21 is a rotary encoder for detecting the position of the stage. The rotary encoder 21 also serves to specify the Y address of the memory. Namely, from the output of the rotary encoder 21, the Y-axis position of the laser beam upon the reticle and pellicle surface can be detected.

Denoted at 30 is the computer, as described, which operates to control the foreign particle inspecting operation as a whole; and at 31 is a console for inputting data into the computer 30. Denoted at 32 is a frequency converting circuit for the counting; at 33 is a frequency converting circuit for the non-counting; at 34 is a selector for selecting the outputs of them; and at 35 is a motor driver for actuating the pulse motor 20. Denoted at 37 and 41 each is a binarizing circuit; at 38 is a delay circuit by which, after elapse of a predetermined time from the detection of the laser beam through the photoelectric converting element 15, the output of a latch circuit 39 is held to "1"; at 40 is a counter for counting the clock pulses CP during a time period when the output of the latch circuit 39 is held at "1". The counter 40 operates also in relation to the X address of the memory, and the X-axis position of the laser beam upon the reticle and pellicle surface is detectable from the output of this counter. The counter 40 is reset when the binarizing circuit 41 produces an output "1". Also, in response to the output of the binarizing circuit 41, the output of the latch circuit 39 is changed to "0".

Figure 2:
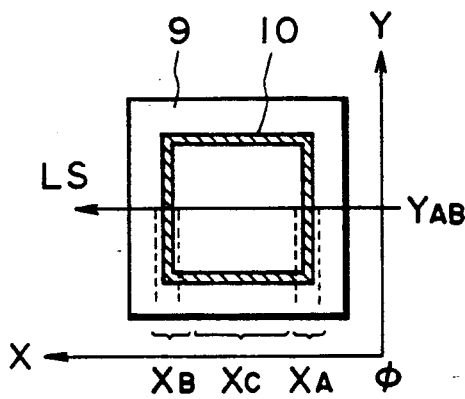
FIG. 2 is a plan view, for explaining the region of laser scanning.

FIG. 2 is a plan view of a reticle 9 having a pellicle, and the coordinates are defined such as shown in FIG. 2. In FIG. 2, reference character LS denotes the direction of laser beam scanning which is parallel to the X-axis. The stage 14 moves in the direction of an arrow S in FIG. 1, namely, in the -Y direction. Accordingly, one scan line of the laser beam projected successively to the reticle 9 with the rotation of the polygonal mirror 2 displaces on the stage 14 in the Y-axis direction. Namely, the laser beam performs "raster scanning" of the reticle and pellicle surface.

Referring now to FIGS. 1 and 2, the foreign particle inspecting operation of the apparatus of the present embodiment will be explained.

In the present embodiment, by moving the stage 14 carrying the reticle 9 thereon in the direction of arrow S, the whole surface of the reticle and pellicle is inspected.

In FIG. 2, the zone depicted by hatching corresponds to the pellicle frame, and in this zone an intense scattered light is produced. In consideration thereof, when the laser beam is scanned with a Y address $Y_{AB}$, within the range of the X addresses $X_A$ and $X_B$, the photomultipliers 7 and 8 are gated to decrease their sensitivities temporarily. Alternatively, the sensitivity of each photomultiplier may be decreased in preparation and, in the range of $X_C$ the sensitivity of each photomultiplier 7 (8) may be increased in response to instructions from the computer 30. When the X address is applied from the counter 40 to the gating control circuit 45 and the Y address is applied thereto from the rotary encoder 21, the X-Y address corresponding to the current position of the beam spot is detected and, according to this address, data regarding whether or not the gating should be made is applied to the gating circuits 43 and 44. In response to such a control signal, the gating circuits 43 and 44 operates to increase/decrease the sensitivities of the photomultipliers 7 and 8.

The data regarding whether the gating is to be made or not, as outputted from the gating control circuit 45 on the basis of the X-Y address, is determined by the position and shape of the pellicle 10 mounted to the reticle 9.

The mounting position has a precision of ±0.5 mm. By executing the gating to such a region wider than the actual frame shape of the pellicle 10, including such a positional deviation, it is possible to protect the photoelectric converting element against intense light.

The data related to the pellicle shape is set into the gating control circuit 45 by the computer 30 in a manner to be described later, and a suitable pellicle shape is selected in accordance with a pellicle 10 mounted to a reticle 9.

While the foregoing description has been made with reference to the pellicle frame of a reticle, the edges (end faces) of the reticle also produce intense scattered light. Thus, the concept of the present invention is effectively applicable to such as edge in a similar manner. Further, the present invention is applicable to an edge of the wafer, other than the reticle, and the present invention is applicable also to a foreign particle inspecting apparatus for a wafer.

In order to preset such a region with respect to which the sensitivity of the photomultiplier tube is to be changed, before the inspection, the whole surface of the object to be inspected is scanned. From the results of such preparative inspection, the zone with respect to which the sensitivity of the photomultiplier tube is to be changed is calculated.

Figure 3:
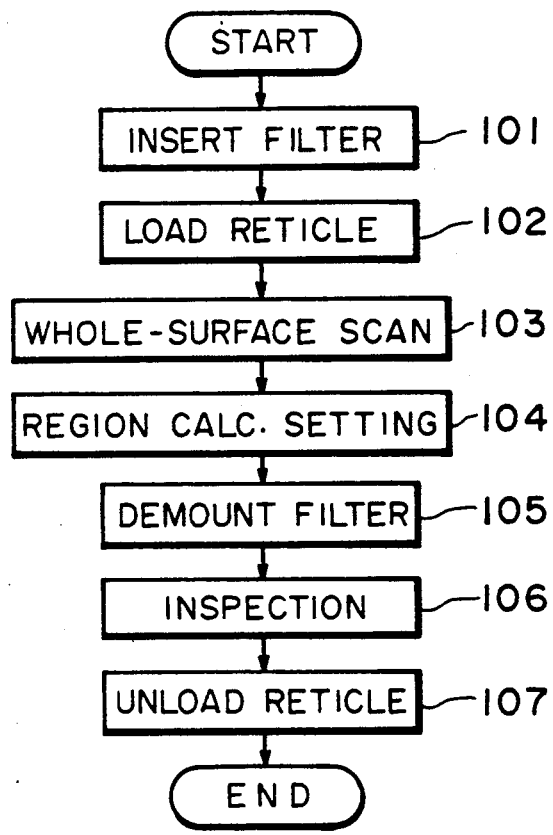
FIG. 3 is a flow chart showing the sequential operation of the inspecting apparatus.

FIG. 3 is a flow chart showing the sequence of inspection according to this method.

In the illustrated sequence, first a filter 46 is inserted into a laser output port so as to reduce scattered light from the pellicle frame (step 101). By this, the intensity of the scattered light from the pellicle frame can be decreased to 1/100 or less, such that damage of the photomultiplier tube can be avoided.

In place of using a filter, a separate photodiode may be used to detect the zone.

Figure 4:
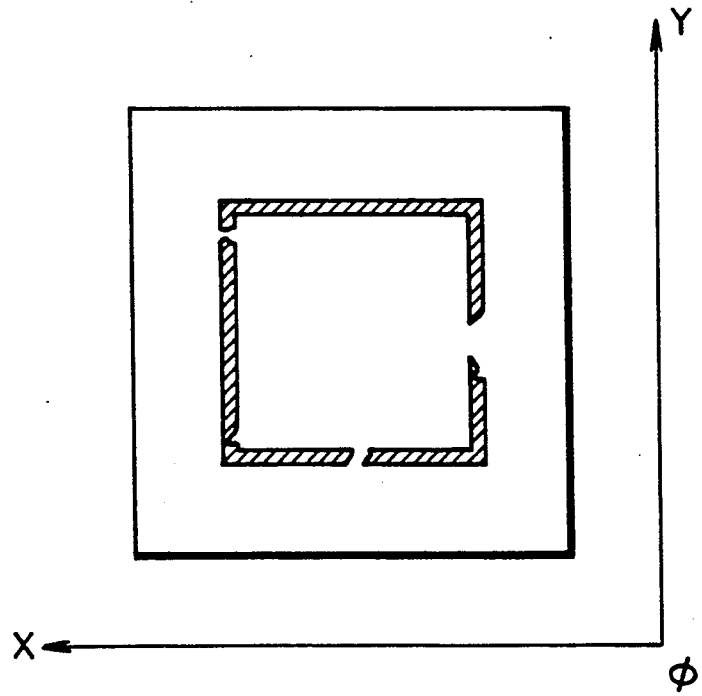
FIG. 4 is a plan view showing a region as calculated by the scanning in the apparatus of FIG. 1.

Next, a reticle is loaded onto the stage 14 (step 102) and the whole surface of the reticle is scanned without gating (step 103). Then, by the discriminating circuit 36, only such data having a voltage not less than a predetermined voltage is selected and, from this data and the address information obtainable from the counter 40 and the rotary encoder 21, the computer 30 calculates the position and shape of the pellicle frame, whereby such data as shown in FIG. 4 is produced.

Since the filter is used, any signal from any foreign particle is so weak that it cannot be discriminated by the discriminating circuit 36. Therefore, only such a portion that produces intense scattered light, with respect to which the sensitivity is to be decreased, can be discriminated. Subsequently, since the pellicle frame has an uninterrupted shape, the computer 30 corrects the obtained data into data such as illustrated in FIG. 2 and sets the same in the gating control circuit 45 (step 104).

Thereafter, the filter 46 is demounted (step 105) and the inspection is performed with the gating based on the set data (step 106). After the inspection is completed, the reticle is unloaded (step 107), such that the inspection sequence is completed.

As described hereinbefore, the inspecting apparatus according to an aspect of the present invention includes first and second position detecting means for detecting the inspection position with respect to the direction of conveyance of an object to be inspected and with respect to the direction of scanning by the inspecting light beam, respectively. Also, on the basis of the output of these position detecting means, in a desired region on the scan line of the light beam, the sensitivity of the photoelectric converting means is changed. Accordingly, it is possible to detect a weak light from a foreign particle while avoiding damage of the photoelectric converting means by intense scattered light or malfunction thereof due to an intense signal.

It is to be noted here that in this Specification the wording "decreasing the sensitivity" means "reducing the output of the photoelectric converter", and clearly this can be done by decreasing the amplification rate of the photomultiplier tube to reduce the ratio of the output to the received light quantity (i.e. to decrease the sensitivity of the photoelectric converting element itself); by inserting a light attenuating means (e.g. a filter) in front of the light receiving port of the photomultiplier tube to thereby reduce or block the light to be reduced; and/or by attenuating or blocking the light being or to be inputted to the reticle. Of course, this may be done by stopping the light emission.

In any case, by reducing the signal light or the ratio of the intensity of an electric signal produced by the signal light, it is possible to prevent production of an excessive or intense electric signal from the photoelectric converter. When the sensitivity of the photoelectric converting element itself is decreased by gating or the like, as regards the light source side, since the state of light emission can be retained unchanged, it is easy to stabilize the characteristics of the light source. Also, it is not necessary to use a mechanism for mounting/demounting the filter or the like. Accordingly, the structure can be simplified.

While the invention has been described with reference to the structures disclosed herein, it is not confined to the details set forth and this application is intended to cover such modifications or changes as may come within the purposes of the improvements or the scope of the following claims.

What is claimed is:

1. An apparatus for inspecting a surface state of a first zone of an article, the article having a second zone which can cause scattering of light stronger than that caused by the first zone, said apparatus comprising:
   a light source for projecting an inspecting light beam to the article;
   a light scanning mechanism for relatively moving the article and the inspecting light beam so as to scan the article with the inspecting light beam;
   a photoelectric converter for detecting light from the article scanned with the inspecting light beam, and for generating an output signal corresponding to the detected light;
   an inspecting device for receiving the output signal from said photoelectric converter, and for determining the surface state of the first zone; and
   a sensitivity controller for relatively decreasing an amplification rate of said photoelectric converter when the second zone is scanned with the inspecting beam in comparison with the amplification rate when the first zone is scanned with the inspecting beam.

2. An apparatus according to claim 1, wherein said photoelectric converter comprises a photomultiplier, and wherein said sensitivity controller decreases the amplification rate of said photoelectric converter through gating of said photomultiplier.

3. An apparatus according to claim 1, further comprising a second zone detecting system for detecting the position of the second zone, wherein said sensitivity controller decreases the amplification rate of said photoelectric converter on the basis of information related to the position of the second zone detected by said second zone detecting system.

4. An apparatus according to claim 3, wherein said second zone detecting system detects the position of the second zone through cooperating of said light source, said light scanning mechanism and said photoelectric converter.

5. An apparatus according to claim 1, wherein said apparatus is used for inspecting a reticle having a pellicle and pellicle frame, and wherein said sensitivity controller decreases the amplification rate of said photoelectric converter when, as the second zone, the pellicle frame and a portion adjacent thereto are scanned with the inspecting beam.

6. An apparatus according to claim 1, wherein said apparatus is used for inspecting a reticle having a pellicle and a pellicle frame, and wherein the sensitivity controller increases the amplification rate of said photoelectric converter when an inside region of the pellicle frame is scanned with the inspecting light beam.

7. An apparatus according to claim 1, wherein said apparatus is used for inspecting a reticle, and wherein said sensitivity controller decreases the amplification rate of said photoelectric converter when, as the second zone, an edge of the reticle is scanned with the inspecting light beam.

8. An apparatus according to claim 1, wherein said apparatus is used for inspecting a wafer, and wherein said sensitivity controller decreases the amplification rate of said photoelectric converter when, as the second zone, an edge of the wafer is scanned with the inspecting light beam.

* * * * *